US010858682B2

(12) United States Patent
Smits et al.

(10) Patent No.: US 10,858,682 B2
(45) Date of Patent: *Dec. 8, 2020

(54) PROCESS FOR ENZYMATIC HYDROLYSIS OF LIGNOCELLULOSIC MATERIAL

(71) Applicant: DSM IP ASSETS B.V., Heerlen (NL)

(72) Inventors: Johannes Petrus Smits, Echt (NL); Michael Petrus Jozef Berkhout, Echt (NL); Bertus Noordam, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/195,608

(22) Filed: Nov. 19, 2018

(65) Prior Publication Data
US 2019/0085366 A1    Mar. 21, 2019

Related U.S. Application Data

(63) Continuation of application No. 14/655,349, filed as application No. PCT/EP2014/050271 on Jan. 9, 2014, now Pat. No. 10,174,351.

(30) Foreign Application Priority Data

Jan. 11, 2013    (EP) .................................. EP13150932

(51) Int. Cl.
*C12P 19/02*    (2006.01)
*C12P 19/14*    (2006.01)
*C13K 1/02*    (2006.01)

(52) U.S. Cl.
CPC ............... *C12P 19/02* (2013.01); *C12P 19/14* (2013.01); *C12Y 302/01004* (2013.01); *C13K 1/02* (2013.01); *C12P 2201/00* (2013.01)

(58) Field of Classification Search
None
See application file for complete search history.

(56) References Cited

U.S. PATENT DOCUMENTS

| | | | |
|---|---|---|---|
| 2008/0044877 A1* | 2/2008 | Penttila | C12P 7/10 435/165 |
| 2009/0098616 A1 | 4/2009 | Burke et al. | |
| 2010/0304437 A1 | 12/2010 | Garner et al. | |
| 2012/0135464 A1 | 5/2012 | Bergsma et al. | |
| 2015/0275255 A1 | 10/2015 | Bergsma et al. | |

FOREIGN PATENT DOCUMENTS

| | | |
|---|---|---|
| CN | 101646767 A | 2/2010 |
| CN | 102740868 A | 10/2012 |
| WO | 2005118828 A1 | 12/2005 |
| WO | 2007091231 A1 | 8/2007 |
| WO | 2008/080093 A2 | 7/2008 |
| WO | 2010/118257 A2 | 10/2010 |
| WO | 2010137039 A2 | 12/2010 |
| WO | 2011000949 A1 | 1/2011 |
| WO | 2011/066457 A2 | 6/2011 |
| WO | 2011080154 A1 | 7/2011 |
| WO | 2012/015605 A1 | 2/2012 |
| WO | 2012/125925 A2 | 9/2012 |

OTHER PUBLICATIONS

Rosgaard et al., Biotechnology Progress, vol. 23, pp. 1270-1276; 2007 (of record). (Year: 2007).*
Szijarto et al., Biotechnology for Biofuels, vol. 4, No. 2, pp. 1 -10, 2011 (of record). (Year: 2011).*
International Search Report from corresponding PCT/EP2014/050271, dated May 30, 2014.
Szijarto et al., "Thermostable endoglucanases in the liquefaction of hydrotherrnally pretreated wheat straw", Biotechnology for Biofuels, 2011, pp. 1-10.
Mesa et al., "Comparison of process configurations for ethanol production from two-step pretreated sugarcane bagasse", Chemical Engineering Journal 175, 2011, pp. 185-191.
Hodge et al., Bioresource Technology, vol. 99, pp. 8940-8948 (electronically available Jun. 26, 2008).
Azevedo, Helena et al., "Possibilities for Recycling Cellulases After Use in Cotton Processing", Applied Biochemistry and Biotechnology, 2002, pp. 77-91, vol. 101, Humana Press Inc.
Lynd, Lee R. et al., "Microbial Cellulose Utiliztion: Fundamentals and Biotechnology", Microbiology and Molecular Biology Reviews, Sep. 2002, pp. 506-577, vol. 66, No. 3.
Sheehan, John et al., "Enzymes, Energy, and the Environment: A Strategic Perspective on the U.S. Department of Energy's Research and Development Activities for Bioethanol", Biotechnology Progress, 1999, pp. 817-827, vol. 15.
Rosgaard et al., Biotechnology Progress, vol. 23, pp. 1270-1276 (2007).

(Continued)

*Primary Examiner* — Soren Harward
*Assistant Examiner* — Paul D Pyla
(74) *Attorney, Agent, or Firm* — McBee Moore & Vanik IP, LLC

(57) ABSTRACT

The invention relates to a process for the hydrolysis of cellulose containing biomass which comprises
a liquefaction step in which a first enzyme or first enzyme composition is added to liquefy at least part of the solids present in the biomass and to keep the viscosity of the cellulose containing biomass below 1000 cP, preferably below 800 cP, more preferably below 600 cP in the liquefaction step; followed by
a saccharification step in which a second enzyme composition is added to form oligomeric and/or monomeric sugars; and
whereby the first enzyme or first enzyme composition is different from the second enzyme composition;
whereby the first enzyme or first enzyme composition comprises an endoglucanase;
whereby the second enzyme composition comprises a cellulase; and
whereby the first enzyme or first enzyme composition comprises more endoglucanase than the second enzyme composition (expressed in protein wt %).

19 Claims, 2 Drawing Sheets

(56) References Cited

OTHER PUBLICATIONS

Viikare, L. et al., "Lignocellulosic ethanol: From science to industry", Biomass and Bioenergy, 2012, pp. 13-24, vol. 46.
Pinheiro Lima, Marco Aurelio et al., "Bioethanol", 2012, pp. 1-290.

\* cited by examiner

PROCESS FOR ENZYMATIC HYDROLYSIS OF LIGNOCELLULOSIC MATERIAL

CROSS REFERENCE TO RELATED APPLICATIONS

This application is a continuation of U.S. patent application Ser. No. 14/655,349, filed 25 Jun. 2015 (now U.S. Pat. No. 10,174,351), which is a § 371 National Stage Application of PCT/EP2014/050271, filed 9 Jan. 2014, which claims priority to EP 13150932.5, filed 11 Jan. 2013. The disclosures of the priority applications are incorporated in their entirety herein by reference.

BACKGROUND

Field of the Invention

The invention relates to a process for the enzymatic hydrolysis of lignocellulosic material.

Description of Related Art

Ligno-cellulosic plant material, herein also called feedstock or cellulose containing material, is a renewable source of energy in the form of sugars that can be converted into valuable products e.g. bio-fuel, such as bio-ethanol. During this process, (ligno or hemi)-cellulose present in the feedstock, such as wheat straw, corn stover, rice hulls, etc., is converted into reducing sugars by (hemi)-cellulolytic enzymes, which then are converted into valuable products such as ethanol by microorganisms like yeast, bacteria and fungi.

Since the (hemi)-cellulose is crystalline and entrapped in a network of lignin, the conversion into reducing sugars is in general slow and incomplete. Typically, enzymatic hydrolysis of untreated feedstock yields sugars <20% of theoretical quantity. By applying a chemical and thermo-physical pre-treatment, the (hemi)-cellulose is more accessible for the (hemi)-cellulolytic enzymes, and thus conversions go faster and at higher yields.

A typical ethanol yield from glucose, derived from pre-treated corn stover, is 40 gallons of ethanol per 1000 kg of dry corn stover (Badger, P, Ethanol from cellulose: a general review, Trends in new crops and new uses. 2002. J. Janick and A. Whipkey (eds.) ASHS Press, Alexandria, Va.), or 0.3 g ethanol per g feedstock. The maximum yield of ethanol on cellulose base is approximately 90%.

Cellulolytic enzymes—most of them are produced by species like *Trichoderma, Humicola* and *Aspergillus*—are commercially used to convert pre-treated feedstock into a mash containing insoluble (hemi)cellulose, reducing sugars made thereof, and lignin. This mash is then used in a fermentation during which the reducing sugars are converted into yeast biomass (cells), carbon dioxide and ethanol. The ethanol produced in this way is called bio-ethanol.

The common production of sugars from pre-treated ligno-celullosic feedstock, the hydrolysis also called liquefaction, pre-saccharification or saccharification, typically takes place during a process lasting 6-168 hours (Kumar, S., Chem. Eng. Technol. 32 (2009) 517-526; Murray, P., et al., Enzyme Microbial Technol 29 (2001) 90-98); under elevated temperatures of 45-50° C. (Kumar, S., Chem. Eng. Technol. 32 (2009) 517-526) and non-sterile conditions. During this hydrolysis, the cellulose present is partly (typically 30-95%, dependable on enzyme activity and hydrolysis conditions) converted into reducing sugars. In case of inhibition of enzymes by compounds present in the pre-treated feedstock and by released sugars; and to minimize thermal inactivation, this period of elevated temperature is minimized as much as possible.

The fermentation following the hydrolysis takes place in a separate anaerobic process step, either in the same or in a different vessel, in which temperature is adjusted to 30-33° C. (mesophilic process) to accommodate growth and ethanol production by microbial biomass, commonly yeasts. During this fermentation process, the remaining (hemi)cellulosic material is converted into reducing sugars by the enzymes already present from the hydrolysis step, while microbial biomass and ethanol are produced. This type of fermentation is therefore often called Simultaneously Saccharification and Fermentation, SSF. The fermentation is finished once (hemi) cellulosic material is converted into fermentable sugars and all fermentable sugars are converted into ethanol, carbon dioxide and microbial cells.

The so obtained fermented mash consists of non-fermentable sugars, non-hydrolysable (hemi) cellulosic material, lignin, microbial cells (most common yeast cells), water, ethanol, dissolved carbon dioxide. During the successive steps, ethanol is distilled from the mash and further purified. The remaining solid suspension is dried and used as, for instance, burning fuel, fertilizer or cattle feed.

With each batch of feedstock, enzymes are added to maximize the yield and rate of fermentable sugars released from the pre-treated ligno-cellulosic feedstock during the given process time. In general, costs for enzymes production, feedstock to ethanol yields and investments are major cost factors in the overall production costs (Kumar, S., Chem. Eng. Technol. 32 (2009) 517-526). Thus far, cost of enzyme usage reduction is achieved by applying enzyme products from a single or from multiple microbial sources (WO2008/008793) with broader and/or higher (specific) hydrolytic activity which use aims at a lower enzyme need, faster conversion rates and/or a higher conversion yields, and thus at overall lower bio-ethanol production costs. This requires large investments in research and development of these enzyme products. In case of an enzyme product composed of enzymes from multiple microbial sources, large capital investments are needed for production of each single enzyme compound.

It is therefore desirable to improve the above process involving hydrolysis and fermentation.

Thermostable cellulolytic enzymes derived from *Talaromyces*, have been used for degrading ligno-cellulosic feedstock and these enzymes are known for their thermostability in WO2007091231. However, no disclosure is given how to optimize the process of hydrolysis and fermentation.

SUMMARY

An object of the invention is to provide a process for the hydrolysis of cellulose containing biomass which comprises
a liquefaction step in which a first enzyme or first enzyme composition is added to liquefy at least part of the solids present in the biomass and to keep the viscosity of the cellulose containing biomass below 1000 cP, preferably below 800 cP, more preferably below 600 cP in the liquefaction step; followed by
a saccharification step in which a second enzyme composition is added to form oligomeric and/or monomeric sugars; and whereby the first enzyme or first enzyme composition is different from the second enzyme composition;

whereby the first enzyme or first enzyme composition comprises an endoglucanase;

whereby the second enzyme composition comprises a cellulase; and whereby the first enzyme or first enzyme composition comprises more endoglucanase than the second enzyme composition (expressed in protein wt %).

Another object of the invention is to provide a process for the hydrolysis of cellulose containing biomass which comprises a liquefaction step in which a first enzyme or first enzyme composition is added to liquefy at least part of the solids present in the biomass and to obtain a viscosity reduction factor of at least 2, at least 4, at least 6, at least 10, at least 15 or at least 20 in the liquefaction step; followed by a saccharification step in which a second enzyme composition is added to form oligomeric and/or monomeric sugars; and whereby the first enzyme or first enzyme composition is different from the second enzyme composition;

whereby the first enzyme or first enzyme composition comprises an endoglucanase;

whereby the second enzyme composition comprises a cellulase; and whereby the first enzyme or first enzyme composition comprises more endoglucanase than the second enzyme composition (expressed in protein wt %).

Preferably the liquefaction step takes place in a reactor (liquefaction reactor) which has a volume smaller than the volume of the reactor (saccharification reactor) in which the saccharification step takes place, preferably the ratio of the volume of the liquefaction reactor and the volume of the saccharification reactor is between 1:2 and 1:50, more preferably between 1:3 and 1:40.

According to another aspect of the invention the liquefaction reactor and/or the saccharification reactor have a volume of more than 1 $m^3$, preferably have a volume of between 10 and 5000 $m^3$.

Advantageously in the liquefaction step or in the liquefaction reactor less enzyme (on protein dry matter) per reactor volume is added than in the step in which the oligomeric and/or monomeric sugar is formed or in the monomeric sugar hydrolysis reactor.

According to a further aspect of the invention the second enzyme composition comprises at least two different cellobiohydrolases and optionally a beta-glucosidase and/or GH61.

Preferably the first enzyme or first enzyme composition and/or the second enzyme or enzyme composition comprises a thermostable enzyme.

According to a preferred embodiment the liquefaction step is done in fed-batch, semi-continuous or continuous mode, more preferably in continuous mode.

According to another preferred embodiment the saccharification step is done in fed-batch, semi-continuous or batch mode, more preferably in batch or fed-batch mode.

In the liquefaction step preferably a dry matter content of 5 wt % or higher, 8 wt % or higher, 10 wt % or higher, 11 wt % or higher, 12 wt % or higher, 13 wt % or higher, 14 wt % or higher, 15 wt % or higher, 20 wt % or higher, 25 wt % or higher, 30 wt % or higher, 35 wt % or higher or 40 wt % or higher and preferably less than 42 wt % is maintained.

The liquefaction step is preferably conducted at a temperature of 50° C. or more, 55° C. or more, 60° C. or more, 65° C. or more, or 70° C. or more preferably the liquefaction step is conducted at a temperature of between 65° C. and 110° C., even more preferably between 65° C. and 90° C., still more preferably between 65° C. and 80° C. and most preferably between 70° C. and 80° C.

DETAILED DESCRIPTION OF A PREFERRED EMBODIMENT

Figure 1:
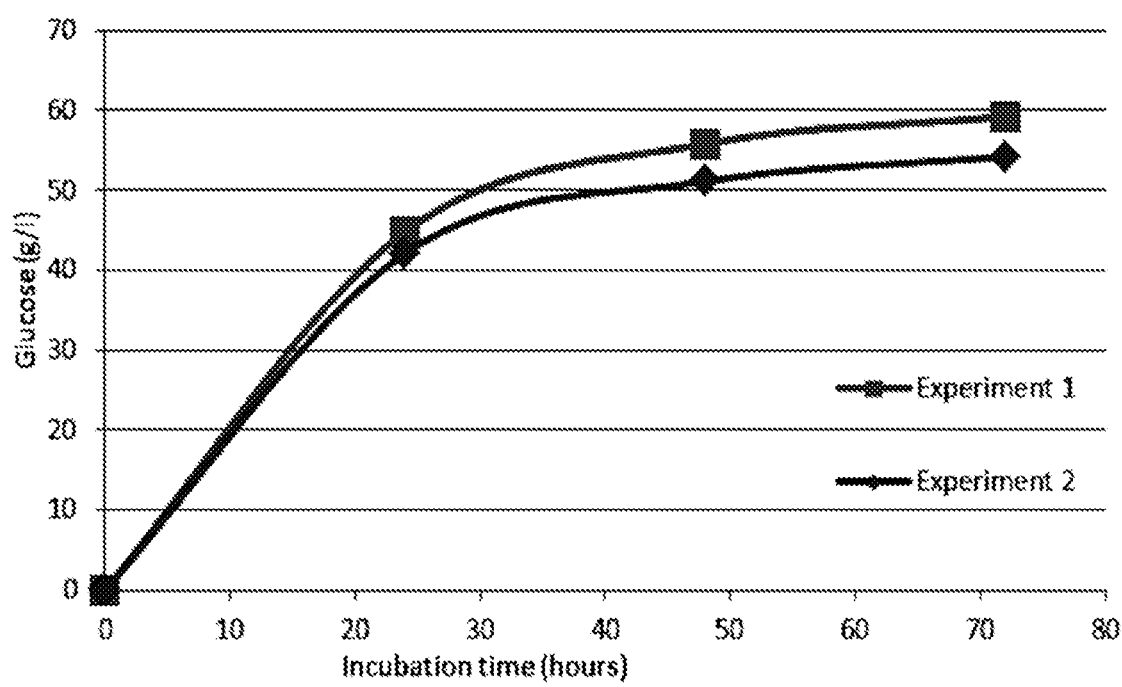
FIG. 1: the effect of preliquefaction with endoglucanase.

The present invention is directed to reduce operational costs such as enzyme costs, reactor costs and energy costs, in a process for the hydrolysis of cellulose containing biomass. Enzyme costs can be reduced by using less enzymes and at same time maintaining high production results such as high levels of sugars, ethanol, biogas or other desired products, all compared to known hydrolysis processes. Reactor cost can be reduced by selecting process conditions which result in lower total reactor volume compared to known hydrolysis processes. Energy savings can be obtained according to the invention by a lower need of energy supply to the process of the invention.

Ligno-Cellulosic Material

Lignocellulosic material herein includes any lignocellulosic and/or hemicellulosic material. Lignocellulosic material suitable for use as feedstock or cellulose containing material in the invention includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, switch grass, miscanthus, corn, corn stover, corn husks, corn cobs, canola stems, soybean stems, sweet sorghum, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforementioned singularly or in any combination or mixture thereof.

Pre-Treatment

The feedstock may optionally be pre-treated with heat, mechanical microbial, enzymatic and/or chemical modification or any combination of such methods in order to to enhance the accessibility of the substrate to enzymatic hydrolysis and/or hydrolyse the hemicellulose and/or solubilize the hemicellulose and/or cellulose and/or lignin, in any way known in the art. In one embodiment, the pretreatment is conducted treating the lignocellulose with steam explosion, hot water treatment or treatment with dilute acid or dilute base.

Washing Step

Optionally, the process according to the invention comprises a washing step. The optional washing step may be used to remove water soluble compounds that may act as inhibitors for the fermentation step. The washing step may be conducted in known manner.

Liquefaction Step

The process according to the invention comprises the liquefaction of the feedstock. In this step optionally pretreated and optionally washed ligno-cellulosic material is brought into contact with a first enzyme or first enzyme composition.

Depending on the lignocellulosic material and the pretreatment, the different reaction conditions, e.g. temperature, enzyme dosage, hydrolysis reaction time and dry matter concentration, may be adapted by the skilled person in order to achieve a desired conversion of lignocellulose. Some indications are given hereafter.

Preferably in the liquefaction step a first enzyme or first enzyme composition is added to liquefy at least part of the solids present in the biomass and to keep the viscosity of the cellulose containing biomass in this step below 1000 cP, preferably below 800 cP, more preferably below 600 cP. The cellulose containing biomass in this step has preferably a dry matter content of between 12 and 35 wt %, more preferably of between 15 and 30 wt %.

At dry matter content of 5 wt % or higher, for example at 20 wt %, cellulose containing biomass will have a viscosity of higher than 1000 cP, for example 2000 cP.

According to another preferred embodiment in the liquefaction step a first enzyme or first enzyme composition is added to liquefy at least part of the solids present in the biomass to obtain a viscosity reduction factor of at least 2, at least 4, at least 6, at least 10, at least 15 or at least 20 in the liquefaction step. In general the viscosity reduction factor will be less than 50. By viscosity reduction factor is meant the viscosity of the biomass which enters the liquefaction step divided by the viscosity of the biomass that leaves the liquefaction step (cP/cP).

In order to obtain high solids content and a low viscosity in the liquefaction step, in the start-up phase the liquefaction reactor may contain water and cellulose containing biomass (and the first enzyme or first enzyme composition) in an amount that the viscosity is lower than 1000 cP, preferably below 800 cP, more preferably below 600 cP. After the viscosity is decreased due to enzyme added, more cellulose containing biomass can be added and thus the dry matter content in the liquefaction step will increase. This start-up procedure can be done until the desired dry matter content in the liquefaction reactor is reached. Subsequently the liquefaction step can be continued in fed-batch, semi-continuous or continuous mode.

Another way of starting up is a procedure wherein the cellulose containing biomass in the liquefaction step has initially a viscosity of higher than 500 cP. In this procedure only after that the first enzyme or first enzyme composition has decreased the viscosity below 1000 cP, preferably below 800 cP, more preferably below 600 cP, the liquefaction step is continued in fed-batch, semi-continuous or continuous mode. In this procedure advantageously in the start-up phase more first enzyme or first enzyme composition is dosed (per dry matter amount of cellulose containing biomass) in the start-up phase than in the subsequent fed-batch, semi-continuous or continuous mode.

The first enzyme or first enzyme composition which is added in the liquefaction step is different from the second enzyme composition used in the saccharification step.

The first enzyme or first enzyme composition comprises an endoglucanase.

The first enzyme or first enzyme composition comprises more endoglucanase than the second enzyme composition (expressed in protein wt %).

In one aspect of the invention the liquefaction step is conducted at a temperature of 50° C. or more, 55° C. or more, 60° C. or more, 65° C. or more, or 70° C. or more preferably the liquefaction step is conducted at a temperature of between 65° C. and 110° C., more preferably between 65° C. and 90° C., still more preferably between 65° C. and 80° C. and most preferably between 70° C. and 80° C. The high temperature during liquefaction has many advantages, which include working at the optimum temperature of the enzyme composition, the reduction of risk of (bacterial) contamination, higher enzyme activity, lower viscosity after the liquefaction step, higher viscosity decay during the liquefaction step, smaller amount of cooling water required, use of cooling water with a higher temperature, re-use of the enzymes is easier and more (all advantages relative to the situation wherein a lower temperature is used in the liquefaction step).

In a further aspect of the invention, the amount of first enzyme or first enzyme composition added (herein also called enzyme dosage or enzyme load) is low. In an embodiment the amount of enzyme added in the liquefaction step is 6 mg protein/g dry matter weight or lower, 5 mg protein/g dry matter or lower, 4 mg protein/g dry matter or lower, 3 mg protein/g dry matter or lower, 2 mg protein/g dry matter or lower, or 1 mg protein/g dry matter or lower (expressed as protein in mg protein/g dry matter). In an embodiment, the amount of enzyme is 0.5 mg enzyme/g dry matter weight or lower, 0.4 mg enzyme composition/g dry matter weight or lower, 0.3 mg enzyme/g dry matter weight or lower, 0.25 mg enzyme/g dry matter weight or lower, 0.20 mg enzyme/g dry matter weight or lower, 0.18 mg enzyme/g dry matter weight or lower, 0.15 mg enzyme/g dry matter weight or lower or 0.10 mg enzyme/g dry matter weight or lower (expressed as total of cellulase enzymes in mg enzyme/g dry matter).

In a further aspect of the invention, the liquefaction time is 10 hours or less, 5 hours or less, 3 hours or less, or 2 hours or less. In another aspect, the liquefaction time is 10 hours to 1 minute, 5 hours to 3 minutes, or 3 hours to 5 minutes. Due to the stability of the enzyme or enzyme composition, the enzyme or enzyme composition will remain active in the next (saccharification) step.

The pH during liquefaction may be chosen by the skilled person. In a further aspect of the invention, the pH during the liquefaction may be 3.0-6.4. The stable enzymes of the invention may be chosen to have a broad pH range of up to 2 pH units, up to 3 pH units, up to 5 pH units. The optimum pH may lie within the limits of pH 2.0 to 8.0, 3.0-8.0, 3.5-7.0, 3.5-6.0 3.5-5.0, 3.5-4.5, 4.0-4.5 or is about 4.2.

Significantly, a process of the invention may be carried out using high levels of dry matter (of the lignocellulosic material) in the liquefaction step. Thus, the invention may be carried out with a dry matter content of 5 wt % or higher, 8 wt % or higher, 10 wt % or higher, 11 wt % or higher, 12 wt % or higher, 13 wt % or higher, 14 wt % or higher, 15 wt % or higher, 20 wt % or higher, 25 wt % or higher, 30 wt % or higher, 35 wt % or higher or 40 wt % or higher and preferably less than 42 wt %. In a further embodiment, the dry matter content in the liquefaction step is 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt % or more or 14-33 wt %.

Preferably the liquefaction reactor has a volume of 1 m$^3$ or more, preferably of more than 10 m$^3$ and most preferably of 50 m$^3$ or more. In general the liquefaction reactor will be smaller than 3000 m$^3$ or 5000 m$^3$ Saccharification The process according to the invention comprises an enzymatic saccharification step. The enzymatic hydrolysis includes, but is not limited to hydrolysis for the purpose of hydrolysis for the purpose of releasing sugar from the liquefied feedstock. In this step optionally pre-treated and optionally washed ligno-cellulosic material is maintained, after liquefaction, into contact with the second enzyme composition.

Depending on the lignocellulosic material, the pre-treatment and liquefaction step, the different reaction conditions, e.g. temperature, enzyme present or optionally dosed, hydrolysis reaction time and dry matter concentration, may be adapted by the skilled person in order to achieve a desired conversion of lignocellulose to sugar. Some indications are given hereafter.

In the saccharification step a second enzyme composition is added to form oligomeric and/or monomeric sugars; and the second enzyme composition comprises a cellulase. The second composition preferably comprises at least two different cellobiohydrolases and optionally a beta-glucosidase and/or GH61.

In one aspect of the invention the saccharification is conducted at a temperature of 50° C. or more, 55° C. or more, 60° C. or more, 65° C. or more, or 70° C. or more. The high temperature during hydrolysis has many advantages, which include working at the optimum temperature of the enzyme composition, the reduction of risk of (bacterial) contamination, smaller amount of cooling water required, use of cooling water with a higher temperature, re-use of the enzymes and more.

In a further aspect of the invention, the amount of second enzyme composition optionally added (herein also called enzyme dosage or enzyme load) is low. In an embodiment the amount of enzyme added in the saccharification step is 6 mg protein/g dry matter weight or lower, 5 mg protein/g dry matter or lower, 4 mg protein/g dry matter or lower, 3 mg protein/g dry matter or lower, 2 mg protein/g dry matter or lower, or 1 mg protein/g dry matter or lower (expressed as protein in mg protein/g dry matter). In an embodiment, the amount of enzyme is 0.5 mg enzyme/g dry matter weight or lower, 0.4 mg enzyme composition/g dry matter weight or lower, 0.3 mg enzyme/g dry matter weight or lower, 0.25 mg enzyme/g dry matter weight or lower, 0.20 mg enzyme/g dry matter weight or lower, 0.18 mg enzyme/g dry matter weight or lower, 0.15 mg enzyme/g dry matter weight or lower or 0.10 mg enzyme/g dry matter weight or lower (expressed as total of cellulase enzymes in mg enzyme/g dry matter). Low enzyme dosage is possible, since because of the activity and stability of the enzymes, it is possible to increase the saccharification reaction time.

In a further aspect of the invention, the saccharification reaction time in the saccharification step is 40 hours or more, 50 hours or more, 60 hours or more, 70 hours or more, 80 hours or more, 90 hours or more, 100 hours or more, 120 hours or more, 130 h or more. In another aspect, the hydrolysis reaction time is 40-130 hours, 50-120 hours, 60-120 hours, 60-110 hours, 60-100 hours, 70-100 hours, 70-90 hours or 70-80 hours. Due to the stability of the enzyme composition longer hydrolysis reaction times are possible with corresponding higher sugar yields.

The pH during hydrolysis in the saccharification step may be chosen by the skilled person. In a further aspect of the invention, the pH during the hydrolysis may be 3.0-6.4. The stable enzymes of the invention may have a broad pH range of up to 2 pH units, up to 3 pH units, up to 5 pH units. The optimum pH may lie within the limits of pH 2.0 to 8.0, 3.0-8.0, 3.5-7.0, 3.5-6.0 3.5-5.0, 3.5-4.5, 4.0-4.5 or is about 4.2.

In a further aspect of the invention the saccharification step is conducted until 70% or more, 80% or more, 85% or more, 90% or more, 92% or more, 95% or more of available sugar in lignocellulosic material is released.

Significantly a process of the invention may be carried out using high levels of dry matter (of the lignocellulosic material) in the saccharification step. Thus, the invention may be carried out with a dry matter content of 5 wt % or higher, 8 wt % or higher, 10 wt % or higher, 11 wt % or higher, 12 wt % or higher, 13 wt % or higher, 14 wt % or higher, 15 wt % or higher, 20 wt % or higher, 25 wt % or higher, 30 wt % or higher, 35 wt % or higher or 40 wt % or higher and preferably less than 42 wt %. In a further embodiment, the dry matter content in the saccharification step is 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt % or more or 14-33 wt %.

Preferably the saccharification reactor has a volume of 1 m$^3$ or more, preferably of more than 10 m$^3$ and most preferably of 50 m$^3$ or more. In general the saccharification reactor will be smaller than 3000 m$^3$ or 5000 m$^3$ Use of Thermostable Enzymes Under Optimal Temperature Conditions In one embodiment, the invention relates to the use of a thermostable enzyme such as cellulolytic enzyme of *Talaromyces* in separate liquefaction and saccharification (SLS) processes for the production of reducing sugars from pretreated ligno-cellulosic feedstock in, but not limiting to, ethanol production. Cellulolytic enzymes of *Talaromyces* applied on pre-treated ligno-cellulosic feedstock showed maximal conversion rates at temperature within the range of 50-70° C. The enzyme remains active under these circumstances for 14 days and more without complete cessation of activity.

By using optimal temperature conditions, maximal amount of reducing sugars can be released from feedstock (total hydrolysis) within the shortest possible hydrolysis time. In this way, 100% conversion of cellulose in glucose is achieved in less than 5 days in an SLS process with an enzyme dosage of 0.175 mL (6 mg protein)/g feedstock dry matter. Under SSF conditions at 33° C. the total conversion of the cellulose in ligno-cellulosic feedstock will last approx. 168 h and herewith these mesophilic conditions determine the process time required for maximal ethanol production from feedstock.

In case thermo stable cellulolytic enzymes, such as from *Talaromyces*, are used in an SSF process with thermophilic ethanol-producing microorganisms, fermentation times will be shorter as cellulolytic enzymes of *Talaromyces* release the reducing sugars faster at higher temperatures than at mesophilic temperatures.

In SSF operation, the product concentration (g/L) is dependent on the amount of glucose produced, but this is not visible since sugars are converted to product in the SSF, and product concentrations can be related to underlying glucose concentration by multiplication with the theoretical maximum yield.

*Rasamsonia* is a new genus comprising thermotolerant and thermophilic *Talaromyces* and *Geosmithia* species (J. Houbraken et al vida supra). Based on phenotypic, physiological and molecular data, Houbraken et al proposed to transfer the species *T. emersonii, T. byssochlamydoides, T. eburneus, G. argillacea* and *G. cylindrospora* to *Rasamsonia* gen. nov. *Talaromyces emersonii, Penicillium geosmithia emersonii* and *Rasamsonia emersonii* are used interchangeably herein.

In one aspect of the invention, the second enzyme composition comprises a cellulase, preferably at least 2 cellulases, more preferably two different cellobiohydrolases and optionally GH61. Preferably at least one, more preferably at least two, even more preferably at least three of the at least three different enzymes are thermostable.

A "thermostable" enzyme means that the enzyme has a temperature optimum 60° C. or higher, for example 70° C. or higher, such as 75° C. or higher, for example 80° C. or higher such as 85° C. or higher. The skilled person may select suitable polynucleotides using common knowledge. They may for example be isolated from thermophilic micro-organisms, or may be designed by the skilled person and artificially synthesized. In one embodiment the polynucleotides may be isolated from thermophilic or thermotolerant filamentous fungi or isolated from non-thermophilic or non-thermotolerant fungi but are found to be thermostable.

Herein, a cellulase is any polypeptide which is capable of degrading or modifying cellulose. A polypeptide which is capable of degrading cellulose is one which is capable of catalysing the process of breaking down cellulose into smaller units, either partially, for example into cellodextrins, or completely into glucose monomers. A cellulase according to the invention may give rise to a mixed population of cellodextrins and glucose monomers when contacted with the cellulase. Such degradation will typically take place by way of a hydrolysis reaction.

GH61 (glycoside hydrolase family 61 or sometimes referred to EGIV) proteins are oxygen-dependent polysaccharide monooxygenases (PMO's) according to the latest literature. Often in literature these proteins are mentioned to enhance the action of cellulases on lignocellulose substrates. GH61 was originally classified as endoglucanase based on measurement of very weak endo-1,4-β-D-glucanase activity in one family member. The term "GH61" as used herein, is to be understood as a family of enzymes, which share common conserved sequence portions and foldings to be classified in family 61 of the well-established CAZY GH classification system a (cazy.org/GH61.html). The glycoside hydrolase family 61 is a member of the family of glycoside hydrolases EC 3.2.1. GH61 is used herein as being part of the cellulases.

Herein, a hemicellulase is any polypeptide which is capable of degrading or modifying hemicellulose. That is to say, a hemicellulase may be capable of degrading or modifying one or more of xylan, glucuronoxylan, arabinoxylan, glucomannan and xyloglucan. A polypeptide which is capable of degrading a hemicellulose is one which is capable of catalysing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers when contacted with the hemicellulase. Such degradation will typically take place by way of a hydrolysis reaction.

Herein, a pectinase is any polypeptide which is capable of degrading or modifying pectin. A polypeptide which is capable of degrading pectin is one which is capable of catalysing the process of breaking down pectin into smaller units, either partially, for example into oligosaccharides, or completely into sugar monomers. A pectinase according to the invention may give rise to a mixed population of oligosacchardies and sugar monomers when contacted with the pectinase. Such degradation will typically take place by way of a hydrolysis reaction.

Herein, a cellobiohydrolase (EC 3.2.1.91) is any polypeptide which is capable of catalysing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

Herein, an endo-β-1,4-glucanase (EC 3.2.1.4) is any polypeptide which is capable of catalysing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

Herein, a β-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

Herein a β-(1,3)(1,4)-glucanase (EC 3.2.1.73) is any polypeptide which is capable of catalyzing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanase when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase; substrates include laminarin, lichenin and cereal beta-D-glucans.

A hemicellulase may be used in the process of the invention, for example, an endoxylanase, a β-xylosidase, a α-L-arabionofuranosidase, an α-D-glucuronidase, an acetyl xylan esterase, a feruloyl esterase, a coumaroyl esterase, an α-galactosidase, a β-galactosidase, a β-mannanase or a β-mannosidase.

Herein, an endoxylanase (EC 3.2.1.8) is any polypeptide which is capable of catalyzing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyse 1,4 xylosidic linkages in glucuronoarabinoxylans.

Herein, a β-xylosidase (EC 3.2.1.37) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, an α-D-glucuronidase (EC 3.2.1.139) is any polypeptide which is capable of catalyzing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. Alternative is EC 3.2.1.131: xylan alpha-1,2-glucuronosidase, which catalyses the hydrolysis of alpha-1,2-(4-O-methyl)glucuronosyl links.

Herein, an acetyl xylan esterase (EC 3.1.1.72) is any polypeptide which is capable of catalyzing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

Herein, a feruloyl esterase (EC 3.1.1.73) is any polypeptide which is capable of catalyzing a reaction of the form: feruloyl-saccharide+H(2)O=ferulate+saccharide. The saccharide may be, for example, an oligosaccharide or a polysaccharide. It may typically catalyze the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

Herein, a coumaroyl esterase (EC 3.1.1.73) is any polypeptide which is capable of catalyzing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

Herein, an α-galactosidase (EC 3.2.1.22) is any polypeptide which is capable of catalyzing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

Herein, a β-galactosidase (EC 3.2.1.23) is any polypeptide which is capable of catalyzing the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

Herein, a β-mannanase (EC 3.2.1.78) is any polypeptide which is capable of catalyzing the random hydrolysis of 1,4-β-D-mannosidic linkages in mannans, galactomannans and glucomannans. This enzyme may also be referred to as mannan endo-1,4-β-mannosidase or endo-1,4-mannanase.

Herein, a β-mannosidase (EC 3.2.1.25) is any polypeptide which is capable of catalyzing the hydrolysis of terminal, non-reducing β-D-mannose residues in β-D-mannosides. This enzyme may also be referred to as mannanase or mannase.

An enzyme composition may comprise any pectinase, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase.

Herein, an endo-polygalacturonase (EC 3.2.1.15) is any polypeptide which is capable of catalyzing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

Herein, a pectin methyl esterase (EC 3.1.1.11) is any enzyme which is capable of catalyzing the reaction: pectin+n H₂O=n methanol+pectate. The enzyme may also been known as pectinesterase, pectin demethoxylase, pectin methoxylase, pectin methylesterase, pectase, pectinoesterase or pectin pectylhydrolase.

Herein, an endo-galactanase (EC 3.2.1.89) is any enzyme capable of catalyzing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

Herein, a pectin acetyl esterase is defined herein as any enzyme which has an acetyl esterase activity which catalyzes the deacetylation of the acetyl groups at the hydroxyl groups of GalUA residues of pectin Herein, an endo-pectin lyase (EC 4.2.2.10) is any enzyme capable of catalyzing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also been known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

Herein, a pectate lyase (EC 4.2.2.2) is any enzyme capable of catalyzing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

Herein, an alpha rhamnosidase (EC 3.2.1.40) is any polypeptide which is capable of catalyzing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

Herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

Herein, exo-galacturonase (EC 3.2.1.67) is any polypeptide capable of catalyzing: $(1,4\text{-}\alpha\text{-D-galacturonide})_n + H_2O = (1,4\text{-}\alpha\text{-D-galacturonide})_{n-1} + \text{D-galacturonate}$. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

Herein, exopolygalacturonate lyase (EC 4.2.2.9) is any polypeptide capable of catalyzing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

Herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

Herein, rhamnogalacturonan lyase is any polypeptide which is any polypeptide which is capable of cleaving α-L-Rhap-(14)-α-D-GalpA linkages in an endo-fashion in rhamnogalacturonan by beta-elimination.

Herein, rhamnogalacturonan acetyl esterase is any polypeptide which catalyzes the deacetylation of the backbone of alternating rhamnose and galacturonic acid residues in rhamnogalacturonan.

Herein, rhamnogalacturonan galacturonohydrolase is any polypeptide which is capable of hydrolyzing galacturonic acid from the non-reducing end of strictly alternating rhamnogalacturonan structures in an exo-fashion.

Herein, xylogalacturonase is any polypeptide which acts on xylogalacturonan by cleaving the β-xylose substituted galacturonic acid backbone in an endo-manner. This enzyme may also be known as xylogalacturonan hydrolase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, endo-arabinanase (EC 3.2.1.99) is any polypeptide which is capable of catalyzing endohydrolysis of 1,5-α-arabinofuranosidic linkages in 1,5-arabinans. The enzyme may also be know as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

An enzyme composition may comprise at least one cellulase and optionally at least one hemicellulase and optionally at least one pectinase (one of which is a polypeptide according to the invention). An second enzyme composition may comprise a GH61, a cellobiohydrolase, an endoglucanase and/or a β-glucosidase. Such a composition may also comprise one or more hemicellulases and/or one or more pectinases.

In addition, one or more (for example two, three, four or all) of an amylase, a protease, a lipase, a ligninase, a hexosyltransferase, a glucuronidase or an expansin or a cellulose induced protein or a cellulose integrating protein or like protein may be used in the process of the invention (these are referred to as auxiliary activities above).

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention incorporated herein by reference. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalyzing a transferase reaction, but which can also catalyze a hydrolysis reaction, for example of cellulose and/or cellulose degradation products. An example of a hexosyltransferase which may be used in the invention is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyaluronoglucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

A composition for use in the invention may comprise an expansin or expansin-like protein, such as a swollenin (see Salheimo et al., Eur. J. Biohem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

In the process of the invention a member of each of the classes of enzymes mentioned above, several members of one enzyme class, or any combination of these enzymes classes or helper proteins (i.e. those proteins mentioned herein which do not have enzymatic activity per se, but do nevertheless assist in lignocellulosic degradation) may be used.

In the process of the invention enzymes may be used from (1) commercial suppliers; (2) cloned genes expressing enzymes; (3) complex broth (such as that resulting from growth of a microbial strain in media, wherein the strains secrete proteins and enzymes into the media; (4) cell lysates of strains grown as in (3); and/or (5) plant material expressing enzymes. Different enzymes in a composition of the invention may be obtained from different sources.

The enzymes can be produced either exogenously in microorganisms, yeasts, fungi, bacteria or plants, then isolated and added, for example, to lignocellulosic feedstock. Alternatively, the enzymes are produced, but not isolated, and crude cell mass fermentation broth, or plant material (such as corn stover or wheat straw), and the like may be added to, for example, the feedstock. Alternatively, the crude cell mass or enzyme production medium or plant material may be treated to prevent further microbial growth (for example, by heating or addition of antimicrobial agents), then added to, for example, a feedstock. These crude enzyme mixtures may include the organism producing the enzyme. Alternatively, the enzyme may be produced in a fermentation that uses (pre-treated) feedstock (such as corn stover or wheat straw) to provide nutrition to an organism that produces an enzyme(s). In this manner, plants that produce the enzymes may themselves serve as a lignocellulosic feedstock and be added into lignocellulosic feedstock.

Fermentation

The process according to the invention may further comprise a fermentation step. In a further aspect, the invention optionally includes a fermentation process in which a microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the lignocellulosic feedstock (e.g. 50 g/l xylose, 35 g/l L-arabinose and 10 g/l galactose. For more dilute sugar compositions the fermentation time may correspondingly be reduced.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, methane or biogas, a β-lactam antibiotics and a cephalosporin. In a preferred embodiment, the fermentation process is anaerobic. An anaerobic process is advantageous since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

The fermentation process is preferably run at a temperature that is optimal for the modified cell. Thus, for most yeasts or fungal cells, the fermentation process is performed at a temperature which is less than 42° C., preferably less than 38° C. For yeast or filamentous fungal host cells, the fermentation process is preferably performed at a temperature which is lower than 35, 33, 30 or 28° C. and at a temperature which is higher than 20, 22, or 25° C.

In an embodiment of the invention, the fermentation is conducted with a microorganism that is able to ferment at least one C5 sugar. In an embodiment the process is a process for the production of ethanol whereby the process comprises the step d) comprises fermenting a medium containing sugar(s) with a microorganism that is able to ferment at least one C5 sugar, whereby the host cell is able to ferment glucose, L-arabinose and xylose to ethanol. In an embodiment thereof the microorganism that is able to ferment at least one C5 sugar is a yeast. In an embodiment, the yeast is belongs to the genus *Saccharomyces*, preferably of the species *Saccharomyces cerevisiae*.

In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

In such process, the volumetric ethanol productivity is preferably at least 0.5, 1.0, 1.5, 2.0, 2.5, 3.0, 5.0 or 10.0 g ethanol per litre per hour. The ethanol yield on L-arabinose and optionally xylose and/or glucose in the process preferably is at least 20, 25, 30, 35, 40, 45, 50, 60, 70, 80, 90, 95 or 98%. The ethanol yield is herein defined as a percentage of the theoretical maximum yield, which, for glucose and L-arabinose and optionally xylose is 0.51 g. ethanol per g. glucose or xylose.

In one aspect, the optional fermentation process leading to the production of ethanol, has several advantages by comparison to known ethanol fermentations processes:
anaerobic processes are possible;
oxygen limited conditions are also possible;
higher ethanol yields and ethanol production rates can be obtained;
the strain used may be able to use L-arabinose and optionally xylose.

Alternatively to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobical or anaerobical conditions, oxygen-limited conditions, temperature at which the process is being carried out, productivity of ethanol, yield of ethanol).

The fermentation process may be carried out without any requirement to adjust the pH during the process. That is to say, the process is one which may be carried out without the addition of any acid(s) or base(s). However, this excludes a pretreatment step, where acid may be added. The point is that the composition of the invention is capable of acting at low pH and, therefore, there is no need to adjust the pH of acid of an acid pretreated feedstock in order that saccharification may take place. Accordingly, a method of the invention may be a zero waste method using only organic products with no requirement for inorganic chemical input.

Overall Reaction Time According to the invention, the overall reaction time (i.e the reaction time of the liquefaction and hydrolysis step, and optionally the fermentation step together may be reduced. In one embodiment, the overall reaction time is 150 hours or less, 140 hours or less, 130 or less, 120 hours or less, 110 hours or less, 100 hours of less, 90 hours or less, 80 hours or less, 75 hours or less, or about 72 hours at 90% glucose yield. Correspondingly lower overall times may be reached at lower glucose yield. This is independent on the mode in which the processes are conducted in SLH mode.

Fermentation Products

Fermentation products which may be produced according to the invention include amino acids, vitamins, pharmaceuticals, animal feed supplements, specialty chemicals, chemical feedstocks, plastics, solvents, fuels such as methane or biogas and ethanol, or other organic polymers, lactic acid, including fuel ethanol (the term "ethanol" being understood to include ethyl alcohol or mixtures of ethyl alcohol and water).

Specific value-added products that may be produced by the methods of the invention include, but not limited to, biofuels (including ethanol and butanol); lactic acid; 3-hydroxy-propionic acid; acrylic acid; acetic acid; 1,3-propanediol; ethylene; glycerol; a plastic; a specialty chemical; an organic acid, including citric acid, succinic acid and maleic acid; a solvent; an animal feed supplement; a pharmaceutical such as a β-lactam antibiotic or a cephalosporin; a vitamin; an amino acid, such as lysine, methionine, tryptophan, threonine, and aspartic acid; an enzyme, such as a protease, a cellulase, an amylase, a glucanase, a lactase, a lipase, a lyase, an oxidoreductase, a transferase or a xylanase; a chemical feedstock; or an animal feed supplement.

Separation of Fermentation Product

The process according to the invention optionally comprises recovery of fermentation product. A fermentation product may be separated from the fermentation broth in any known manner. For each fermentation product the skilled person will thus be able to select a proper separation technique. For instance ethanol may be separated from a yeast fermentation broth by distillation, for instance steam distillation/vacuum distillation in conventional way.

Certain embodiments of the invention will below be described in more detail, but are in no way limiting the scope of the present invention.

Enzyme Recycling after Hydrolysis with Stable Enzymes

At the end of the hydrolysis, enzyme activities appear to be low since little reducing sugars are released once almost all cellulose is converted. The amount of enzymatic activity present, however, has decreased only a little, assumingly mainly due to absorption of the enzymes to the substrate. By applying solid-liquid separation after hydrolysis, such as centrifugation, filtration, sedicantation, etcetera, 60% or more e.g. 70% of the enzyme activity in solution can be recovered and re-used for liquefaction or hydrolysis of a new pre-treated ligno-cellulosic feedstock during the next hydrolysis.

Moreover, after solid-liquid separation the enzyme in solution can be separated from the solution containing reducing sugars and other hydrolysis products from the enzymatic actions. This separation can be done by, but not limiting to, (ultra and micro)filtration, centrifugation, sedicantation, sedimentation, with or without first adsorption of the enzyme to a carrier of any kind.

For example, after hydrolysis of pre-treated feedstock with 0.175 mL/g feedstock dry matter enzyme load for 20 h, 50% of the theoretical maximum amount of reducing sugars is liberated and after the same hydrolysis for 72 h, 90% of the theoretical maximum amount of reducing sugars is liberated. By centrifugation and ultrafiltration, 60-70% of the enzyme activity was recovered in the retentate, while the filtrate contained more than 80% of the liberated reducing sugars. By re-using the retentate, either as it is or after further purification and/or concentration, enzyme dosage during the next hydrolysis step can be reduced with 60-70%. The cost reduction achieved by using stable cellulolytic enzymes, such as of *Talaromyces*, in this way results from requiring less enzyme dosage.

Enzyme Recycling after Liquefaction with Stable Enzymes

At the end of the liquefaction, the enzymes used in the liquefaction can be recycled in a similar way as described hereinabove for the recycling after hydrolysis (liquefaction and saccharification).

Enzyme Recycling after Hydrolysis in Combination with Enzyme Production and Yeast-Cell Recycling with Stable Enzymes The process including enzyme recycling after hydrolysis, as described above, can be combined with recycling of the ethanol producing microorganism after fermentation and with the use of the reducing sugars containing filtrate as a substrate (purified and/or concentrated or diluted) in enzyme-production fermentation and as substrate for the cultivation of the ethanol-producing microorganism.

Enzyme Recycling after Vacuum Distillation with Stable Enzymes

The thermo stability of enzymes, like those from *Talaromyces*, causes remaining cellulolytic activity after hydrolysis, fermentation and vacuum distillation in the thin stillage. The total activity of the enzyme is reduced during the three successive process steps with 10-15 Substrate units per g dry-matter feedstock, independently of the initial enzyme dosage. The thin stillage obtained after vacuum distillation can thus be re-used as a source of enzyme for a newly started hydrolysis-fermentation-distillation process cycle of pretreated wheat straw conversion into ethanol. The thin stillage can be used either in concentrated or (un)diluted form and/or purified and with or without additional enzyme supplementation. Thin stillage, optionally purified, can be re-used for liquefaction or hydrolysis of cellulosic material.

The invention is further described by the following examples, which should not be construed as limiting the scope of the invention.

EXAMPLES

Materials & Methods
Viscosity Determination

The RVA (Rapid Visco Analyser) measurement was performed using the Newport RVA-4 rapid viscosity analyzer equipped with a plastic paddle (see: D. L. Goode et al, Journal of the Institute of Brewing, Vol. 111, No. 2, 2005).

Enzymes

TEC-210 cellulase composition was fermented according to the inoculation and fermentation procedures described in WO2011/000949.

*Rasamsonia* (*Talaromyces*) *emersonii* strain was deposited at CENTRAAL BUREAU VOOR SCHIMMELCULTURES, Uppsalalaan 8, P.O. Box 85167, NL-3508 AD Utrecht, The Netherlands in December 1964 having the Accession Number CBS 393.64.

Other suitable strains can be equally used in the present examples to show the effect and advantages of the invention. For example TEC-101, TEC-147, TEC-192, TEC-201 or TEC-210 are suitable *Rasamsonia* strains which are described in WO2011/000949.

Endoglucanase (EG) is produced by overexpression of EBA8 in *Aspergillus niger* as described in WO2011/098577 followed by fermentation of the *Aspergillus niger* transformant. EBA8 is a *Rasamsonia emersonii* (*Talaromyces emersonii*) endoglucanase and is identified in WO2011/098577 as *T. emersonii* beta-glucanase CEA (EG) and represented by SEQ ID NO: 3 in WO2011/098577.

Preparation of Acid Pre-Treated Corn Stover Substrate.

Dilute-acid pre-treated corn stover (aCS) was obtained as described in Schell, D. J., Applied Biochemistry and Biotechnology (2003), vol. 105-108, pp 69-85. A pilot scale pretreatment reactor was used operating at steady state conditions of 190° C., 1 min residence time and an effective $H_2SO_4$ acid concentration of 1.45% (w/w) in the liquid phase.

Example 1

The Effect of the Endoglucanase During Hydrolysis of Linoceilloluse Feedstock

The effect of endoglucanase during hydrolysis of lignocellulose feedstock is described according to the procedures described below. The hydrolysis reactions were performed with acid pretreated cornstover (aCS) feedstock. The pH of the feedstock was adjusted to pH 4.5 with a 4M NaOH solution. The hydrolysis reaction was carried out in two stages:

1. A liquefaction step operated in a semi continuous mode.
2. A saccharification step operated in batch mode.

The liquefaction was conducted as follows: a liquefaction reactor was filled with 1 kg of 10% (w/w) pretreated cornstover feedstock. The reactor was operated under constant stirring, pH control (pH 4.5, 4N NaOH) and 62° C. Directly after filling, enzyme was dosed (see Table 1) to start the hydrolysis reaction. Next, every 10 minutes an additional amount of 55 g of feedstock of 30% dry matter was added to the liquefaction reactor under constant bleeding of reactor content in order to keep the reactor filling level constant at 1 litre. In addition, extra enzyme was dosed together with the additional feedstock to maintain a constant enzyme/substrate ratio during the reaction. After about 3 hours a dry matter level of about 20% (w/w) was reached in the reactor and the dry matter of the feedstock to add, was reduced to 20% (w/w) to keep the dry matter level in the reactor at about 20% (w/w). 6 hours after start of the liquefaction, the bleed of the liquefaction reactor was introduced into a saccharification reactor for further processing. The residence time in the liquefaction reactor was on average about 3 hours.

The saccharification was conducted as follows: a saccharification reactor was filled with the bleed form the liquefaction reactor to a total reaction volume of about 1 litre. This took about 3 hours. The reactor was operated under constant stirring, pH control (pH 4.5, 4N NaOH) and 62° C. During filling enzyme was added simultaneously in one of the experiments as is visualized in Table 1. The saccharification reaction was conducted for about 70 hours.

TABLE 1 enzyme dosing scheme

| | Liquefaction | | Saccharifacation | |
|---|---|---|---|---|
| Experiment | Endoglucanase | Cellulase cocktail | Endoglucanase | Cellulase cocktail |
| 1 | 1 mg/g | — | — | 4 mg/g |
| 2 | 1 mg/g | 4 mg/g | — | — |

Cellulase cocktail: TEC-210
Endoglucanase: EBA8
Enzyme dosage: mg TCA protein per gram of feedstock dry matter Following hydrolysis, the samples were cooled on ice and immediately 50 µl of each supernatant was diluted in 1450 µl grade I water. The diluted supernatant was subsequently filtered (0.45 µm filter, Pall PN 454) and the filtrates were analysed for sugar content as described below.

The sugar concentrations of the diluted samples were measured using an HPLC equipped with an Aminex HPX-87P column (Biorad #1250098) by elution with water at 85° C. at a flow rate of 0.6 ml per minute and quantified by integration of the glucose signals from refractive index detection (R.I.) calibrated with glucose standard solutions.

The data presented in FIG. 1 show that the glucose release from the feedstock pretreated with endoglucanase is faster and results in a higher level (for example after 72 hours) than the glucose released from the feedstock where endoglucanase and the TEC-210 cellulase enzyme cocktail were added at the same time.

Based on these results it was concluded that liquefaction of lignocellulose feedstock with an endoglucanase containing enzyme composition improves the cellulolytic performance of cellulase mixtures.

Example 2

The Effect of the Endoglucanase in the Liquefaction Step

Samples of 20% dry-matter pretreated feedstock (acid pretreated cornstover) of pH 4.5 in water were pre-heated at 62° C. in the Newport RVA-4 for one hour at low stirring rate. Enzyme was added on time=0 of the measurement and the viscosity decrease was recorded at 62° C. during the succeeding two hours, and registered by a computer attached.

The results presented in Table 2 show that EG (EBA8) improved the viscosity reduction for the biomass substrate as well as that a batch start-up procedure can be used to start up the process of the invention.

TABLE 2

|  | Time when 4000 cP is reached (s) | Time when 2000 cP is reached (s) | Timev when 1000 cP is reached (s) | Time when 500 cP is reached (s) |
|---|---|---|---|---|
| 1.0 mg TEC-210/g TS |  | 3000 | 4000 |  |
| (0.5 mg TEC-210 + 0.5 mg EG)/g TS |  | 500 | 2500 | 3620 |
| 2.0 mg TEC-210/g TS | 500 | 2000 |  |  |
| (1.0 mg TEC-210 + 1.0 mg EG)/g TS | 100 | 400 |  |  |

Example 3

The Effect of Temperature on the Liquefaction of Lignocellolosic Feedstock

The effect of temperature on the liquefaction of lignocellulosic feedstock by endoglucanase is demonstrated by this experiment. The liquefaction experiments were performed using acid pretreated corn stover feedstock (aCS) obtained from NREL (National Renewable Energy Laboratory).

Samples of 24% dry matter pretreated feedstock of pH 4.5 in water were pre-heated in the Newport RVA-4 for one hour at low stirring rate. Enzyme (0.2 mg EG [EBA8] per gram of dry matter) was added on time=0 of the measurement and the viscosity decrease was recorded during the succeeding 60 minutes and registered by a computer attached. Incubations were conducted at 62, 70 and 75° C.

Figure 2:
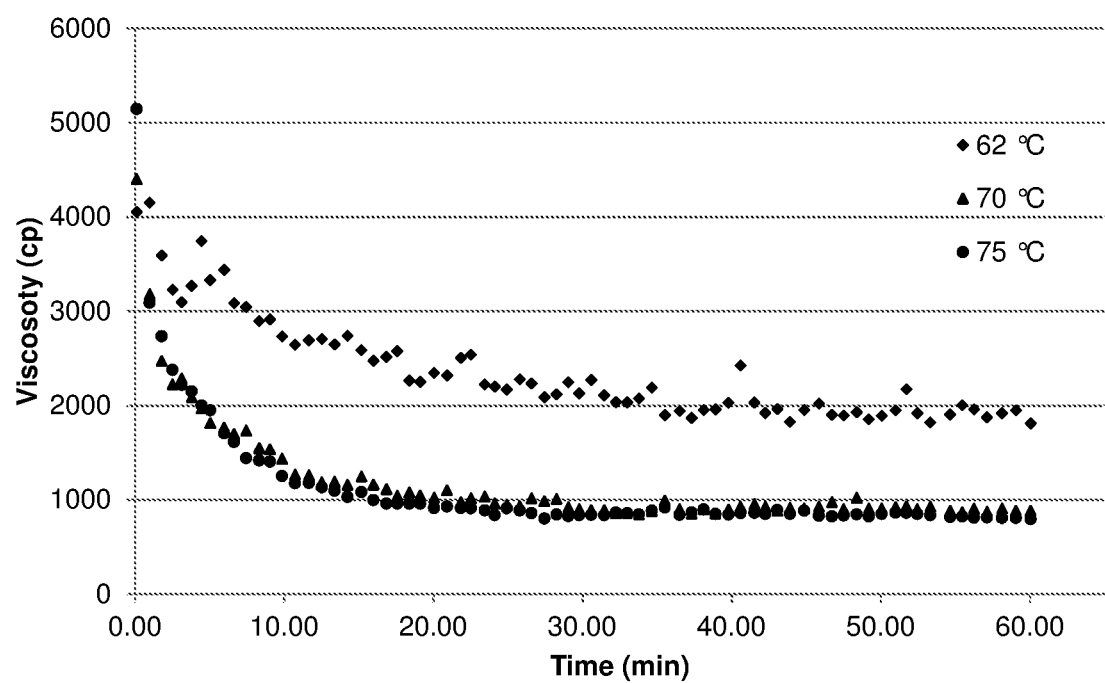
FIG. 2: viscosity decay during liquefaction of lignocellulosic feedstock at different temperatures (♦=62° C., ▲=70° C. and ●=75° C.).

The results presented in FIG. 2 show that EG (EBA8) can liquefy lignocellulosic feedstock at temperatures up to 75° C. and that higher temperatures result in lower viscosity.

The invention claimed is:

1. A process for the hydrolysis of cellulose containing biomass, wherein the cellulose containing biomass includes lignocellulosic and hemicellulosic material, said process comprising:
   a liquefaction comprising adding a first enzyme or first enzyme composition to the biomass to liquefy at least part of the solids present in the biomass and to obtain a viscosity reduction factor of at least 2 in the resulting liquefied biomass; followed by
   a saccharification comprising adding to the liquefied biomass a second enzyme composition to form oligomeric and/or monomeric sugars; and
   whereby the first enzyme or first enzyme composition is different from the second enzyme composition;
   whereby the first enzyme or first enzyme composition comprises an endoglucanase;
   whereby the second enzyme composition comprises a beta-glucosidase, GH61, endoglucanase, and at least two different cellobiohydrolases; and
   whereby the first enzyme or first enzyme composition comprises more endoglucanase than the second enzyme composition, expressed in protein wt %;
   whereby the dry matter content in the liquefaction is 15 wt % or higher.

2. The process according to claim 1, whereby the liquefaction takes place in a liquefaction reactor which has a volume, and the saccharification takes place in a saccharification reactor which has a volume, wherein the liquefaction reactor volume is smaller than the saccharification reactor volume.

3. The process according to claim 2, wherein the ratio of the volume of the liquefaction reactor and the volume of the saccharification reactor is between 1:2 and 1:50.

4. The process according to claim 2, whereby the liquefaction reactor and/or the saccharification reactor have a volume of more than 1 m$^3$.

5. The process according to claim 1, whereby:
   a) less enzyme per reactor volume is added to the liquefaction reactor than is added to the saccharification reactor; or
   b) less enzyme is added to the liquefaction than is added to the saccharification;
   wherein the amount of enzyme is measured as mg enzyme/g dry matter weight.

6. The process according to claim 1, whereby the first enzyme or first enzyme composition and/or the second enzyme or enzyme composition comprises a thermostable enzyme.

7. The process according to claim 1, whereby the liquefaction is done in fed-batch, semi-continuous or continuous mode.

8. The process according to claim 1, whereby the liquefaction is done in continuous mode.

9. The process according to claim 1, whereby the saccharification is done in fed-batch, semi-continuous or batch mode.

10. The process according to claim 1, whereby the saccharification is done in fed-batch or batch mode.

11. The process according to claim 1, whereby the dry matter content in the liquefaction is 20 wt % or higher.

12. The process according to claim 1, whereby the dry matter content in the liquefaction is between 15 wt % and 42 wt %.

13. The process according to claim 1, whereby the liquefaction is conducted at a temperature of 50° C. or more.

14. The process according to claim 1, whereby the liquefaction time is 10 hours or less.

15. The process according to claim 1, whereby the saccharification time is 40 hours or more.

16. The process according to claim 1, further comprising a fermentation.

17. The process according to claim 11, whereby the fermentation is conducted with a microorganism that is able to ferment at least one C5 sugar.

18. The process of claim 1, wherein the first enzyme or first enzyme composition consists essentially of an endoglucanase.

19. The process of claim 1, whereby the saccharification is conducted until at least 70% of available glucose in the cellulose containing biomass is released.

* * * * *